United States Patent
Sato et al.

(10) Patent No.: US 6,332,868 B1
(45) Date of Patent: Dec. 25, 2001

(54) METHOD FOR EVALUATING SKIN CONDITIONS

(75) Inventors: Makoto Sato; Kunihiro Murata, both of Tochigi; Yasushi Shioya; Yoshiaki Fujikura, both of Ichikai-machi, all of (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/500,543

(22) Filed: Feb. 9, 2000

(30) Foreign Application Priority Data

Feb. 12, 1999 (JP) .................................................. 11-034681

(51) Int. Cl.[7] .................................................. A61B 05/00
(52) U.S. Cl. .................................................. 600/306
(58) Field of Search .......................... 600/306, 473–478; 128/897–8

(56) References Cited

U.S. PATENT DOCUMENTS

| | | | |
|---|---|---|---|
| 4,528,986 | * 7/1985 | Arundel et al. .................... | 600/473 |
| 5,348,002 | * 9/1994 | Caro .................................... | 600/310 |
| 5,615,675 | * 4/1997 | O'Donnell et al. ................. | 600/473 |
| 5,845,640 | * 12/1998 | Lawandy ............................. | 600/473 |

* cited by examiner

*Primary Examiner*—Robert E. Nasser, Jr.
(74) *Attorney, Agent, or Firm*—Oblon, Spivak, McClelland, Maier & Neustadt, P.C.

(57) ABSTRACT

The invention relates to a method for evaluating skin conditions, which comprises applying at least two chemical substances to the skin, measuring amounts of said at least two chemical substances penetrated into the skin and calculating out the ratio between the amounts penetrated into the skin; and a kit for evaluating skin conditions, comprising a reagent containing at least two chemical substances and a measuring device of amounts of the chemical substances penetrated into the skin, wherein said at least two chemical substances are applied to the skin, amounts of said at least two chemical substances penetrated into the skin are measured by means of the measuring device, and the ratio between the amounts penetrated into the skin is calculated out.

12 Claims, 7 Drawing Sheets

1 A
1 0 A. Opto-acoustic cell

Fig. 1

10A. Opto-acoustic cell

METHOD FOR EVALUATING SKIN CONDITIONS

BACKGROUND OF THE INVENTION

Field of the Invention

1. The present invention relates to a method for evaluating skin conditions and a kit for evaluating skin conditions.

2. Description of the Background Art

It is known that skin conditions has a close relationship to the barrier function of a horny layer, and the lowering of the barrier function brings on deterioration of the skin conditions, such as skin roughness. An amount of water volatilized out of the interior of the body through the skin (transepidermal water loss, TWL) is used as an index to such barrier function. It is said that TWL increases as the barrier function deteriorates. However, TWL is not always highly correlated with the barrier function of the horny layer. The reason for it is that the deterioration of the barrier function of the horny layer for stimuli and allergens is not grasped as the amount of substances penetrated into the interior from the exterior of the skin.

Accordingly, it is considered that the skin conditions can be exactly evaluated by determining the penetrability (percutaneous absorptivity) of substances into the skin. It is known that the penetrability of substances into the skin can be determined by the opto-coustic method, chromatographic method, absorptiometric ethod, etc.

However, the amount of a chemical substance penetrated into the skin varies according to factors such as the temperature and humidity of the chemical substance and skin, the amount of the chemical substance applied to the skin, and an application method, and it is technically difficult to conduct the measurement with such factors kept completely constant. Therefore, it has been extremely difficult to evaluate the skin conditions from the measured value of the penetrated amount, since an error in measurement is great. Accordingly, there has been a demand for development of a method for evaluating skin conditions, by which physiological skin conditions can be digitized.

SUMMARY OF THE INVENTION

The present inventors have found that when amounts of at least two chemical substances penetrated into the skin are measured, and the ratio between the amounts penetrated into the skin is found, the above-described factors of the error in the measurement of the amount penetrated into the skin, such as temperature and application method, are offset, and so the ratio can be calculated out with high precision, and consequently the ratio has extremely high correlation with the skin conditions.

According to the present invention, there are thus provided a method for evaluating skin conditions, which comprises applying at least two chemical substances to the skin, measuring amounts of said at least two chemical substances penetrated into the skin and calculating out the ratio between the amounts penetrated into the skin, and a kit for the evaluation.

When the method or kit according to the present invention is used, skin conditions can be evaluated with ease.

DETAILED DESCRIPTION OF THE DRAWINGS

In the drawings, reference characters and numerals have the following respective meanings:

1A, 1C, 1D: an apparatus for measuring amounts of chemical substances penetrated into the skin;
2: an opening;
3: a housing;
4: an LED;
5: a microphone;
6: a quartz window;
7: a microphone chamber;
8: an irradiation chamber;
9: a communication hole;
10A: an optic-acoustic cell; and
S: the skin.

DETAILED DESCRIPTION OF THE PREFERRED EMBODIMENTS

In the evaluating method according to the present invention, at least two chemical substances are first applied to the skin. The skin may be any part of the body. The chemical substances include those described in Standard for Raw Materials of Cosmetics, and the like. Said at least two chemical substances may be any substances so far as they are different from each other in physical properties. The physical properties as used herein mean properties of a chemical substance, by which the penetrability of the chemical substance into the skin is affected, and examples thereof include solubility in solvents, molecule weight, ionicity, partition properties (log P) in water/an oily substance, pKa, pH, adsorptivity on the skin and viscosity of a solution of the chemical substance. Among these, the solubility in solvents, molecular weight, ionicity, pKa or pH is preferred from the viewpoint of easy measurement.

As combinations of such at least two chemical substances, are mentioned combinations of, for example, coloring matters different from each other in solubility in ethanol and water when the physical property is the solubility in solvents, with a combination of Yellow Color No. 4 and Red Color No. 215 being particularly preferred. When the physical property is log P, examples thereof include a combination of 1,3-butanediol and glycerol-1-benzyl-3-n-hexyl diether which are different from each other in partition coefficient in water/an oil-soluble substance. In this case, one substance desirably has log P not higher than 3. When the physical property is the molecular weight, examples thereof include combinations among riboflavin (Rf), flavin adenine dinucleotide (FAD) and flavin adenine mononucleotide (FMN).

In actual measurement, it is preferred to uniformly mix at least two chemical substances and optionally dissolving them in a proper solvent to apply them to the skin in the form of a mixed solution from the viewpoint of elimination of the factors of the error in the measurement of amounts penetrated into the skin. When at least three chemical substances are applied at the same time, the precision is enhanced.

The amounts of said at least two chemical substances penetrated (penetrated amounts per unit area) are then measured. No particular limitation is imposed on the time from the application of the chemical substances up to the measurement so far as it is fixed. For example, 0.5 to 30 minutes are preferred. As a measuring method, is preferred the opto-acoustic method, chromatographic method or absorptiometric method. In the chromatographic method and absorptiometric method, a portion of the skin is peeled by a method such as tape stripping, the chemical substances penetrated into the skin are extracted with a proper solvent, and measurement is conducted in accordance with a method known per se in the art. Examples of the chromatographic method include adsorption chromatography, thin-layer chromatography, gel filtration chromatography and liquid chromatography. It is necessary to select an analytic means depending on chemical substances measured.

The ratio between the amounts penetrated into the skin is then calculated out. Although the measured values obtained by this method are opto-acoustic signal strengths (the amounts penetrated into the skin have extremely high correlation with the opto-acoustic signal strengths) when the opto-acoustic method is used as the measuring method of the amounts penetrated into the skin, the opto-acoustic signal strengths may not be converted into the amounts penetrated into the skin because the ratio between them is calculated out after the measurement of the penetrated amounts. The same applies to the chromatographic method and absorptiometric method. The opto-acoustic method is particularly preferred in that the amounts penetrated into the skin can be measured directly in vivo. The opto-acoustic method is a measuring method in which a substance to be measured generates heat by absorbing light struck, and a pressure wave (acoustic wave) generated by the heat is detected. A measuring apparatus (opto-acoustic cell) for the opto-acoustic method is described in detail in, for example, Japanese Patent Application Laid-Open No. 292327/1998 the disclosure of which is incorporated herein by reference and made a part of this application. Such an opto-acoustic cell is brought into contact with the applied site of the skin, and modulation frequency, excitation wavelength and half band width are suitably selected to irradiate the applied site with light, whereby an opto-acoustic signal strength can be measured. This value can provide the amount penetrated into the skin. The thickness of the horny layer is generally 10 to 50 $\mu$m, and the modulation frequency is desirably 5 to 800 Hz. As a light source for the excitation light of the measuring apparatus in the opto-acoustic method, is mentioned an Xe—Hg lamp, halogen lamp, light emitting diode (LED) or laser. Among these, the use of the light emitting diode (LED) is particularly preferred because the system can be markedly miniaturized and lightened to make the measuring apparatus portable, and intermittent light can be obtained with ease by modulation making use of an oscillating circuit to make the control of modulation frequency easy, whereby an S/N ratio can be markedly improved compared with the conventional ratio obtained by mechanically forming intermittent light by a chopper.

More specifically, as the measuring apparatus of the amounts of chemical substances penetrated into the skin used in the present invention, is preferred a measuring apparatus of the amounts of chemical substances penetrated into the skin, comprising an irradiating means for irradiating the skin with excitation light, and a detecting means for detecting opto-acoustic signals produced from the skin, wherein LED is used as a light source of the excitation light.

The present invention will hereinafter be described in detail by embodiments using the opto-acoustic method with reference to the drawings. In the drawings, like reference characters designate like or corresponding components throughout.

Figure 1:
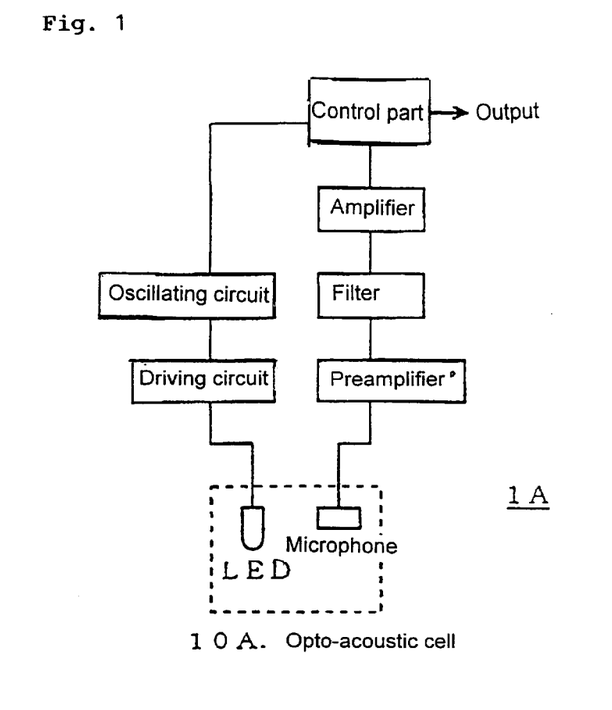
FIG. 1 illustrates a block diagram of an apparatus for measuring amounts of chemical substances penetrated into the skin according to the present invention.
Figure 2:
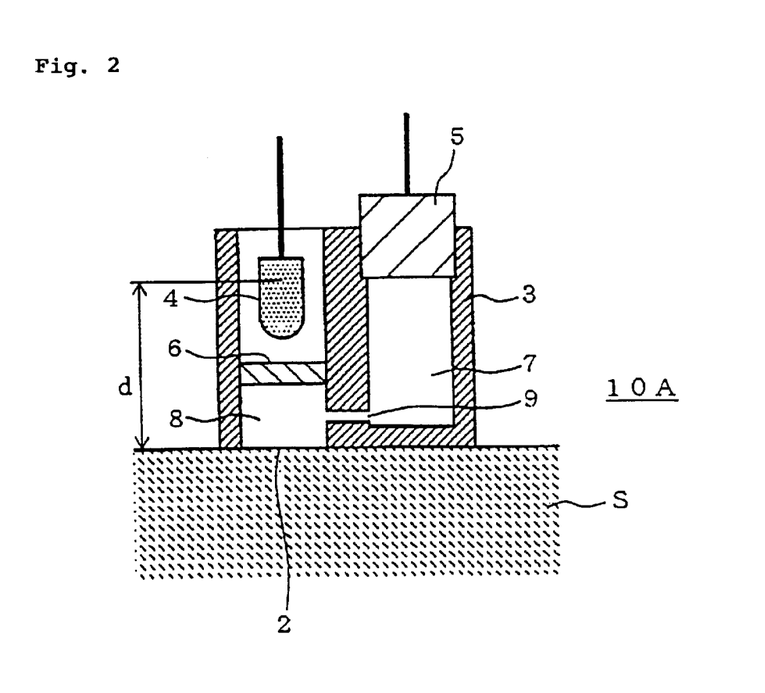
FIG. 2 is a cross-sectional view of an opto-acoustic cell.

FIG. 1 illustrates a block diagram of an apparatus 1A for measuring amounts of chemical substances penetrated into the skin according to an embodiment of the present invention, and FIG. 2 is a cross-sectional view of an opto-acoustic cell 10A used in the measuring apparatus 1A.

The opto-acoustic cell 10A noninversively measures the amount of a substance in the skin S and is hence an opto-acoustic cell of the open type that an opening 2 of the cell is pressed against the skin S to conduct measurement. In the interior of a housing 3, are provided an LED 4 and a microphone 5. The inner wall surface of the housing 3 in which the LED 4 has been provided is planished, and the skin S is irradiated with light emitted from the LED 4 through all over the opening 2 through a quartz window 6. The microphone 5 is installed in a microphone chamber 7 as described in Japanese Patent Application Laid-Open No. 292327/1998 for the purpose of preventing the mixing of noises from the surroundings to improve an S/N ratio, and the microphone chamber 7 is communicated with an irradiation chamber 8 having the opening 2 through a communication hole 9.

As the LED, is preferred an LED the wavelength of light emitted from which conforms to an absorption spectrum of a substance to be measured as much as possible in that sensitomety is enhanced, and LEDs of various luminescent colors may be used depending on substances to be measured.

The mere provision of the LED in the opto-acoustic cell 10A has a possibility that sufficient light intensity may not be attained on the surface of the skin S to be irradiated to low the strength of the resulting opto-acoustic signals. In order to enhance the strength of the opto-acoustic signals, it is considered to widen an irradiation area on the skin S. When an irradiation angle is widened to widen the irradiation area, however, a luminous flux diffuses to weaken the intensity of light on the surface to be irradiated, so that the skin S cannot be irradiated with excitation light with sufficient strength after all. In order to cope with this, it is considered to provide an optical system that the diffused luminous flux is converged. However, the provision of such an optical system prevents the miniaturization and weight-saving of the apparatus. In the opto-acoustic cell 10A of this measuring apparatus, it is thus preferred that a distance d from the emission center of the LED to the skin S and a diameter of the site of the skin S to be irradiated be adjusted to 3 to 16 mm and 2 to 8 mm, respectively. This adjustment permits the excitation light emitted from the LED to effectively irradiate the skin S.

A control part is realized by a personal computer on a hardware basis to control modulation frequency produced by the oscillating circuit according to the prescribed measurement depth, and the LED is constant-current driven at the modulation frequency produced by the oscillating circuit to emit continuous modulated light.

Figure 7:
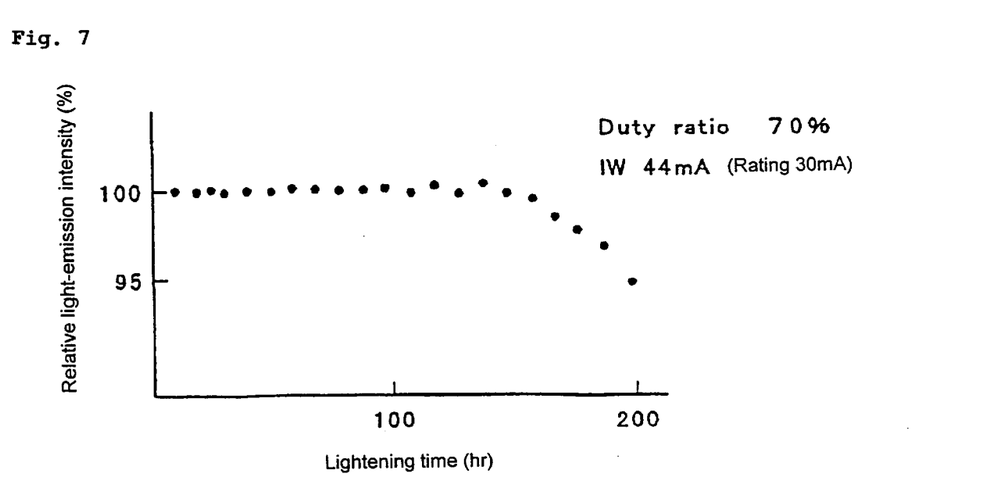
FIG. 7 diagrammatically illustrates the relationship between lighting time of LED and relative emission intensity.
Figure 8:
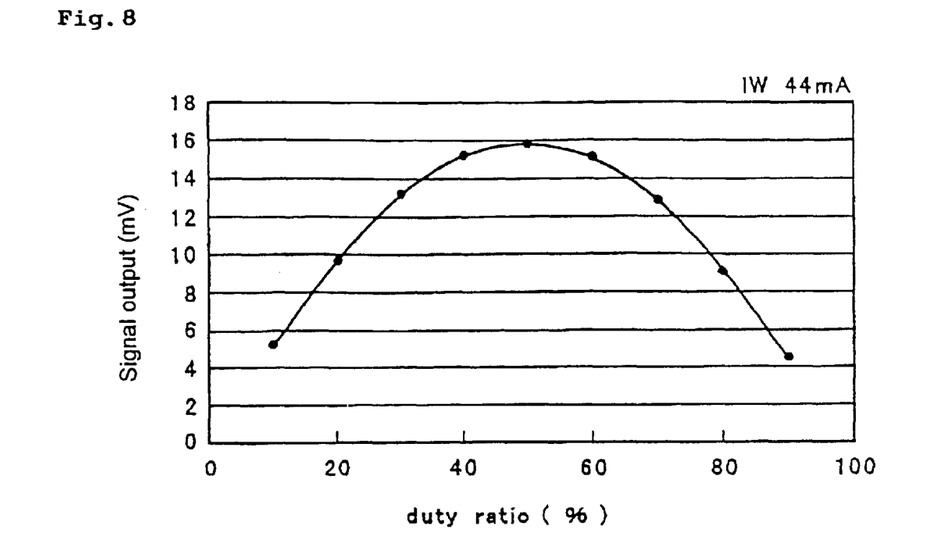
FIG. 8 diagrammatically illustrates the relationship between the duty ratio of LED upon driving and opto-acoustic signals.

In a drive circuit, it is preferred to drive the LED in such a manner that the duty ratio (on/off ratio) of the LED is 30 to 70%. More specifically, it is considered to raise the duty ratio in order to enhance the light intensity of the excitation light. However, the LED is broken if the duty ratio is raised higher than the rating. On the other hand, when the duty ratio is controlled to 70% or lower, the LED stably emits light over a period as long as 200 hours as illustrated in FIG. 7. When the stable emission time of the LED is 200 hours, the measurement may be performed at least 120,000 times because the measuring time of percutaneous absorption per time is about 6 seconds.

On the other hand, the opto-acoustic signal becomes high at the duty ratio of 30 to 70% and maximum at 50%. Accordingly, the duty ratio is preferably controlled to 30 to 70% from the viewpoints of long-time stability to operation of the LED and the strength of the opto-acoustic signal.

The microphone 5 detects an acoustic wave generated by the skin S irradiated with the excitation light emitted from the LED. The acoustic wave signal detected by the microphone 5 is amplified by a preamplifier, and an acoustic wave signal corresponding to the modulation frequency is separated by a filter and further amplified by an amplifier to send it the control part. The control part conducts arithmetic processing such as Fourier transformation and lock-in processing to output an opto-acoustic signal. The arithmetic processing may be conducted in accordance with an analytic technique for the publicly known photoacoustic spectrometry [for example, Japanese Patent Application Laid-Open No. 160711/1998; and K. KOLMEL, J. Soc. Cosmt. Chem., 37, 375 (1986)].

According to the measuring apparatus 1A, the apparatus can be miniaturized and lightened because the LED is used as a light source for the excitation light in place of an Xe-Hg lamp or the like conventionally used. In addition, the S/N ratio can be enhanced because the excitation light is not mechanically intermitted by a chopper, but the emission of the LED is electronically intermitted by the modulation frequency. Further, light modulation at high frequency and low frequency is also facilitated.

Figure 3:
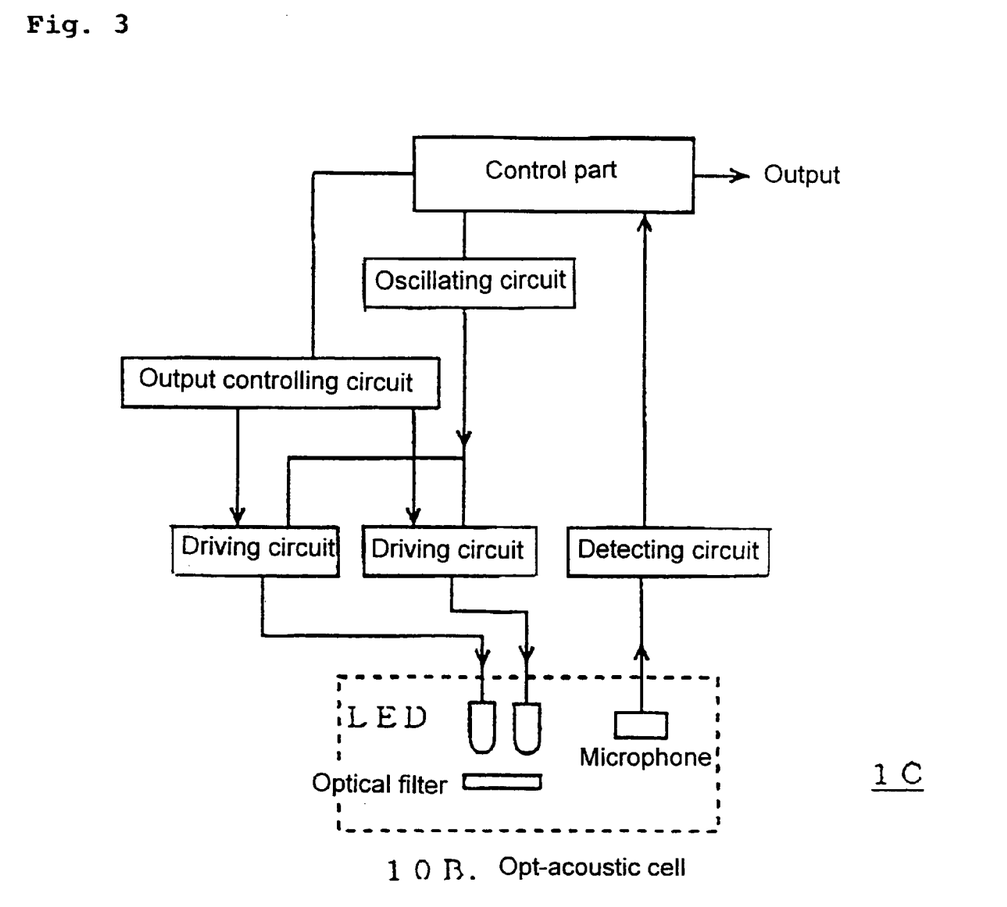
FIGS. 3 and 4 respectively illustrate block diagrams of measuring apparatus according to the present invention.

FIG. 3 illustrates a block diagram of an apparatus 1C for measuring amounts of chemical substances penetrated into the skin according to another embodiment of the present invention. In the measuring apparatus 1C, 2 LEDs the emission spectra of which overlap with each other are provided adjoiningly to each other, an output controlling circuit for controlling the output of the respective LEDs is provided, and an optical filter which passes light within the prescribed wavelength range is further provided in front of the two LEDs. According to this measuring apparatus 1C, therefore, the two LEDs can be caused to emit at the same time while controlling the output of the LEDs, so as to irradiate the skin with light passed through the optical filter in the form of excitation light, so that the emission spectrum of excitation light can be brought close to an absorption spectrum characteristic of its corresponding substance to be measured. Namely, the emission spectrum of the excitation light irradiated on the skin from an LED is preferably adjusted to the absorption spectrum of a substance to be measured from the viewpoint of enhancing the precision of measurement. However, LEDs have their inherent emission spectra depending on the kinds thereof, so that the emission spectrum of an LED may not conform to an absorption spectrum of the intended substance to be measured, and an S/N ratio may be hence lowered in some cases.

When an amount of, for example, coloring matter penetrated into the horny layer of the skin is measured, the opto-acoustic signal strength of the horny layer itself, into which the coloring matter is not penetrated, is first measured, and the coloring matter is then penetrated into the horny layer to measure an opto-acoustic signal strength, thereby finding an amount of the coloring matter penetrated into the horny layer from a difference between both opto-acoustic signal strengths. However, when the opto-acoustic signal strength of the horny layer itself is high, and the absorption spectrum of the coloring matter is different from the emission spectrum of the LED, the precision of measurement is lowered because the increment of signal strength by the coloring matter compared with the signal strength by the horny layer lessens.

In such a case, in this measuring apparatus 1C, 2 LEDs the peaks of emission spectra of which are respectively located before and after the peak of the absorption spectrum of the coloring matter, and overlap with each other are selected to cause these LEDs to emit at the same time while controlling the output of the LEDs, and rays emitted from the two LEDs pass through an optical filter which passes rays within the absorption spectral range of the coloring matter. In such a manner, light having a synthetic spectrum of the emission spectra of the two LEDs, the peak wavelength of which conforms to the peak wavelength of the absorption spectrum of the coloring matter, and the half band width of which is narrowed, can be obtained as excitation light, whereby the signal strength by the coloring matter can be greatly enhanced. In this technique, the number of emission spectra of LEDs to be used in the synthesis is not limited to 2, and a plurality of LEDs may be suitably used.

Figure 4:
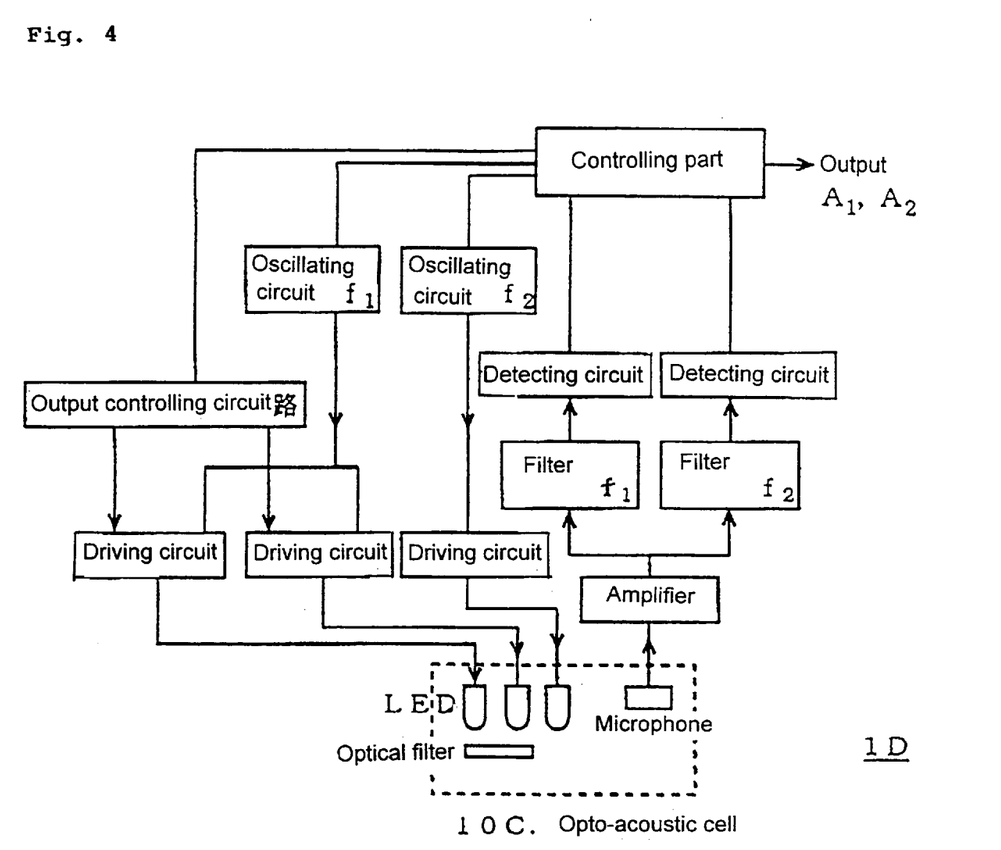

FIG. 4 illustrates a measuring apparatus 1D in which the technique of the measuring apparatus 1A illustrated in FIG. 1 and the measuring apparatus 1C illustrated in FIG. 3 are combined with each other as a means for irradiating with excitation light.

In the measuring apparatus of the amounts of chemical substances penetrated into the skin according to the present invention, as described above, a plurality of LED may be independently used as a means for irradiating with excitation light, or a synthetic spectrum of spectra of a plurality of LEDs may be used, depending on the number of substances to be measured and absorption spectra thereof. When the wavelengths of absorption spectra of the substances to be measured are different from each other, their determination can be performed at the same time by varying the wavelengths of rays respectively emitted from LEDs.

Since the ratio thus obtained can offset influence by temperature and the like, an error in measurement is very small. Therefore, such a ratio has extremely high correlation with skin conditions and is useful in evaluating the skin conditions.

The kit for diagnosing skin conditions according to the present invention comprises a reagent containing said at least two chemical substances different in physical properties and a measuring device of amounts of the chemical substances penetrated into the skin. When measurement is conducted in vivo, examples of the measuring device of the amounts penetrated into the skin include an opto-acoustic cell (including the case where LED(s) are used as a light source) described in Japanese Patent Application Laid-Open No. 292327/1998, and the like. When a portion of the skin is peeled and the chemical substances penetrated into the skin are measured by extraction or the like, a chromatograph such as HPLC, an absorbance measuring device and the like are mentioned. Such a kit is used to calculate out the ratio between the amounts penetrated into the skin in accordance with the above-described method, whereby the skin conditions can be evaluated.

EXAMPLE 1 AND COMPARATIVE EXAMPLE 1

After an ethanol solution of Yellow Color No. 4 (tartrazine, wavelength of absorption spectrum: 425 nm; 1.57 mmol·dm$^{-3}$) was penetrated for 2 minutes into the skin of the human forearm, an opto-acoustic signal was measured by means of the apparatus 1A illustrated in FIG. 1. In this case, modulation frequency, the wavelength of light emitted from the LED and light intensity per unit area were controlled to 410 Hz, 460 nm (half band width: 21 nm) and 2 mw/cm$^2$, respectively. The same measurement was conducted 20 times to find an average value x of the opto-acoustic signals and a standard deviation σ thereof (Example 1).

A photoacoustic spectrometer using an Xe—Hg lamp as a light source was used to conduct the same measurement (Comparative Example 1). In this case, light intensity per unit area was controlled to the same level as in Example 1.

The results are shown in Table 1.

TABLE 1

|  | Ex. 1 | Comp. Ex. 1 |
| --- | --- | --- |
| Opto-acoustic signal strength (average value x) | 1.1626 mV | 1.166 mV |
| Standard deviation σ | 0.0178 mV | 0.0379 mV |

From Table 1, it is understood that the standard deviation in the case where the LED is used as a light source is smaller than that in the case where the Xe—Hg lamp is used as a light source when the intensity of irradiation in both cases is the same, and so the precision of measurement is improved.

EXAMPLE 2

The measuring apparatus illustrated in FIG. 3 was used to first measure an opto-acoustic signal of the skin (horny layer) of the human forearm, and Red Color No. 215 (wavelength of absorption spectrum: 545 nm; 2 mmol·dm$^{-3}$) was penetrated for 2 minutes into the same site, thereby finding opto-acoustic signal strengths of the horny layer before and after the penetration of the coloring matter to determine an opto-acoustic signal strength by the coloring mater by subtracting the former opto-acoustic signal strength from the latter opto-acoustic signal strength.

Figure 5:
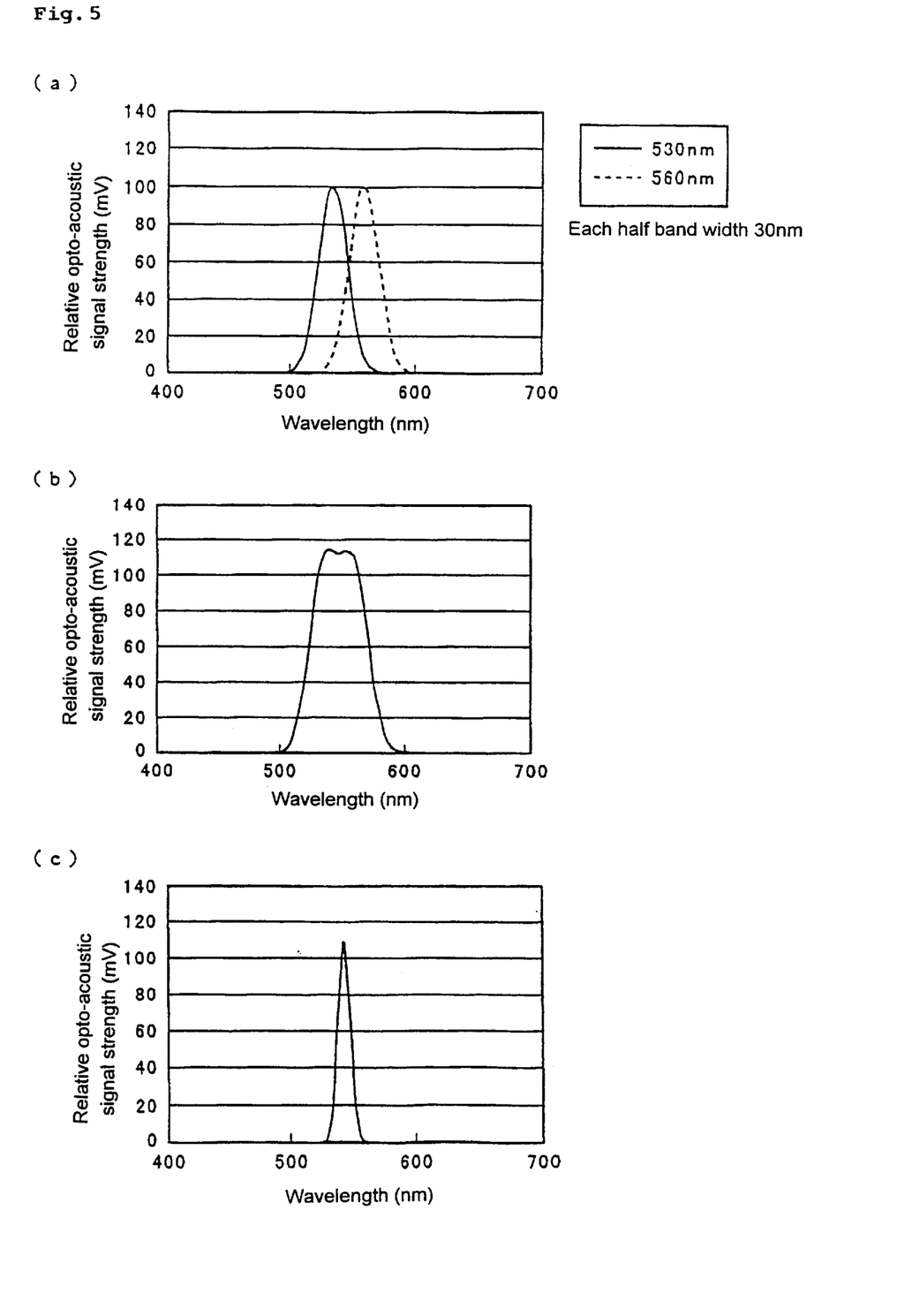
FIGS. 5A, 5B and 5C illustrate an emission spectrum of an LED, a synthetic spectrum of emission spectra of two LEDs and a synthetic spectrum after passing through an optical filter, respectively.

In this case, that having an emission spectrum (wavelength of light emitted: 530 nm; half band width: 30 nm) illustrated by a solid line in FIG. 5A and that having an emission spectrum (wavelength of light emitted: 560 nm; half band width: 30 nm) illustrated by a broken line in the same drawing were used as LEDs to obtain a spectrum (peak wavelength: 545 nm) illustrated in FIG. 5B as a synthetic spectrum thereof. An interference filter was further used as an optical filter having a center frequency of 545 nm and a half band width of 15 nm, thereby obtaining a spectrum illustrated in FIG. 5C. Light of this spectrum was used as excitation light to measure the opto-acoustic signal strength. For the sake of comparison, an opto-acoustic signal strength in the case where light emitted from one LED (wavelength of light emitted: 530 nm; half band width: 30 nm) was used as excitation light as it was also measured. The results are shown in Table 2.

TABLE 2

| | Opto-acoustic signal strength [mV] | | |
| --- | --- | --- | --- |
|  | Horny layer | Horny layer + coloring matter | Coloring matter |
| Excitation light by synthetic spectrum (wavelength of light emitted: 545 nm; half band width: 15 nm) | 0.581 | 1.0 | 0.419 |
| Excitation light by single LED (wavelength of light emitted: 530 nm; half band width: 30 nm) | 0.915 | 1.0 | 0.085 |

From Table 2, it Is understood that a spectrum is synthesized from the emission spectra of LEDs to cause the emission spectrum of excitation light to conform to the absorption spectrum of the coloring matter, thereby improving the detection precision of the coloring matter.

EXAMPLE 3

Sample solutions prepared by mixing two substances [Yellow Color No. 4 (wavelength of absorption spectrum: 425 nm) and Red Color No. 215 (wavelength of absorption spectrum: 545 nm)] different in absorption spectrum at varied concentrations were separately penetrated for 2 minutes into the human forearm to simultaneously conduct the quantitative analyses of these two substances by means of the measuring apparatus illustrated in FIG. 4.

In this case, an LED which emits light having a wavelength of 460 nm was driven at modulation frequency of 423 Hz for the detection of Yellow Color No. 4, while a synthetic spectrum of light having a wavelength of 546 nm was obtained from LEDs which respectively emit rays having a wavelength of 530 nm and a wavelength of 560 nm, and this light was used to conduct measurement for the detection of Red Color No. 215.

Figure 6:
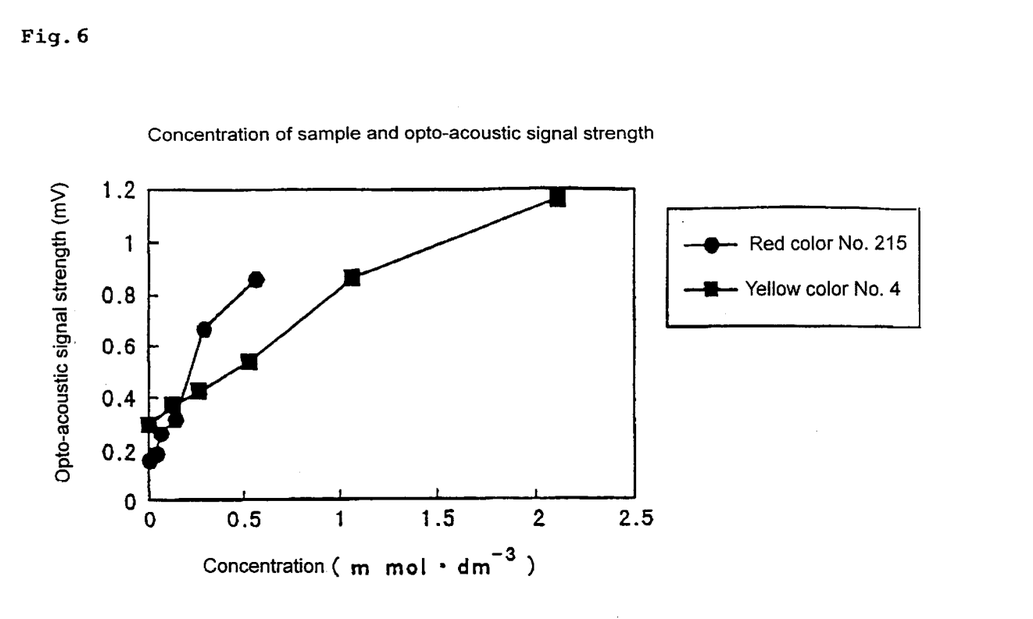
FIG. 6 diagrammatically illustrates the relationship between adjusted concentrations of samples and opto-acoustic signal strength.

The detection results of the respective coloring matters are shown in Table 3 and FIG. 6.

TABLE 3

| Concentration of sample prepared (mmol · dm$^{-3}$) | | Opto-acoustic signal strength (mV) | |
| --- | --- | --- | --- |
| Red Color No. 215 | Yellow Color No. 4 | Red Color No. 215 | Yellow Color No. 4 |
| 0.560 | 2.110 | 0.871 | 1.1624 |
| 0.280 | 1.055 | 0.672 | 0.8674 |
| 0.140 | 0.528 | 0.321 | 0.5526 |
| 0.070 | 0.264 | 0.265 | 0.4262 |
| 0.035 | 0.132 | 0.191 | 0.3794 |
| 0.000 | 0.000 | 0.175 | 0.3016 |

From Table 3 and FIG. 6, it Is understood that many components can be simultaneously separated and determined by an optical difference between wavelengths of the respective absorption spectra.

EXAMPLE 4

Hydrophilic Yellow Color No. 4 which has solubility of 0.05 mol·dm$^{-3}$ in ethanol and solubility of 0.33 mol·dm$^{-3}$ in water, and amphipathic Red Color No. 215 which has solubility of 0.2 mol·dm$^{-3}$ in ethanol and solubility of 0.23 mol·dm$^{-3}$ in water were dissolved in ethanol to give concentrations of 0.05 mol·dm$^{-3}$ and 0.2 mol·dm$^{-3}$, respectively, thereby preparing a mixed solution. The mixed solution was applied to each 5 sites of the forearms of 3 healthy persons and 2 patients suffering from atopic dermatitis in an amount of 20 μl per cm$^2$. After 2 minutes, opto-acoustic signals were measured by means of the measuring apparatus 1D illustrated in FIG. 4. In this case, the measurement was conducted at modulation frequency of 410 Hz. With respect to the wavelengths of rays emitted from LEDs, for the detection of Red Color No. 215, a synthetic spectrum of light having a wavelength of 546 nm (half band width: 10 nm) was obtained in accordance with the technique described in Example 2 from LEDs which respectively emit rays having a wavelength of 530 nm and a wavelength of 560 nm, while for the detection of Yellow Color No. 4, an LED which emits light having a wavelength of 460 nm (half band width: 10 nm) was used. The intensity of light per unit area was controlled to 0.5 Mw/cm$^2$ to measure opto-acoustic signals from the surface of the skin up to 15 μm in depth. The measurement was performed 5 times to find an average value $x_1$ of the opto-acoustic signals and a standard deviation $\sigma_1$, thereof. The results are shown in FIG. 9.

With respect to each subject, the ratio [signal strength ratio (Yellow/Red)] $x_2$ between the opto-acoustic signal strength of Yellow Color No. 4 and the opto-acoustic signal strength of Red Color No. 215, and a standard deviation $\sigma_2$ thereof were found. The results are shown in FIG. 10.

Figure 9:
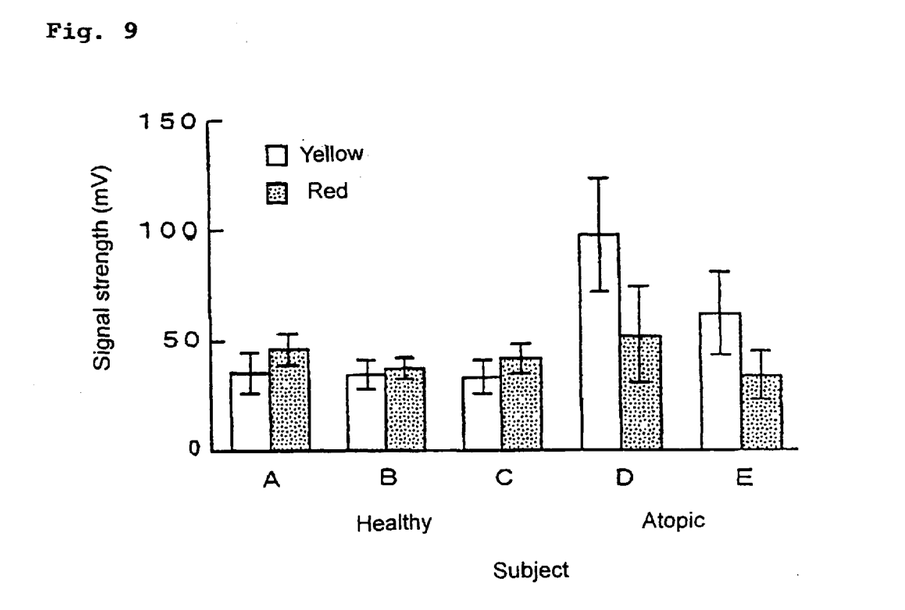
FIG. 9 diagrammatically illustrates average values of opto-acoustic signal strengths as to individual subjects and standard deviations a thereof (in the drawing, 2σ is represented by I)

As apparent from FIG. 9, there was no difference among all the subjects as to $x_1$ of Red Color No. 215. With respect to Yellow Color No. 4, $x_1$ of the patients suffering from atopic dermatitis was higher than that of the healthy persons, but $\sigma_1$ was very great, and $x_1-\sigma_1$ of the subject E was smaller than each $x_1+\sigma_1$ of the three healthy persons. Accordingly, it is difficult to evaluate skin conditions from the signal strengths of the respective coloring matters.

Figure 10:
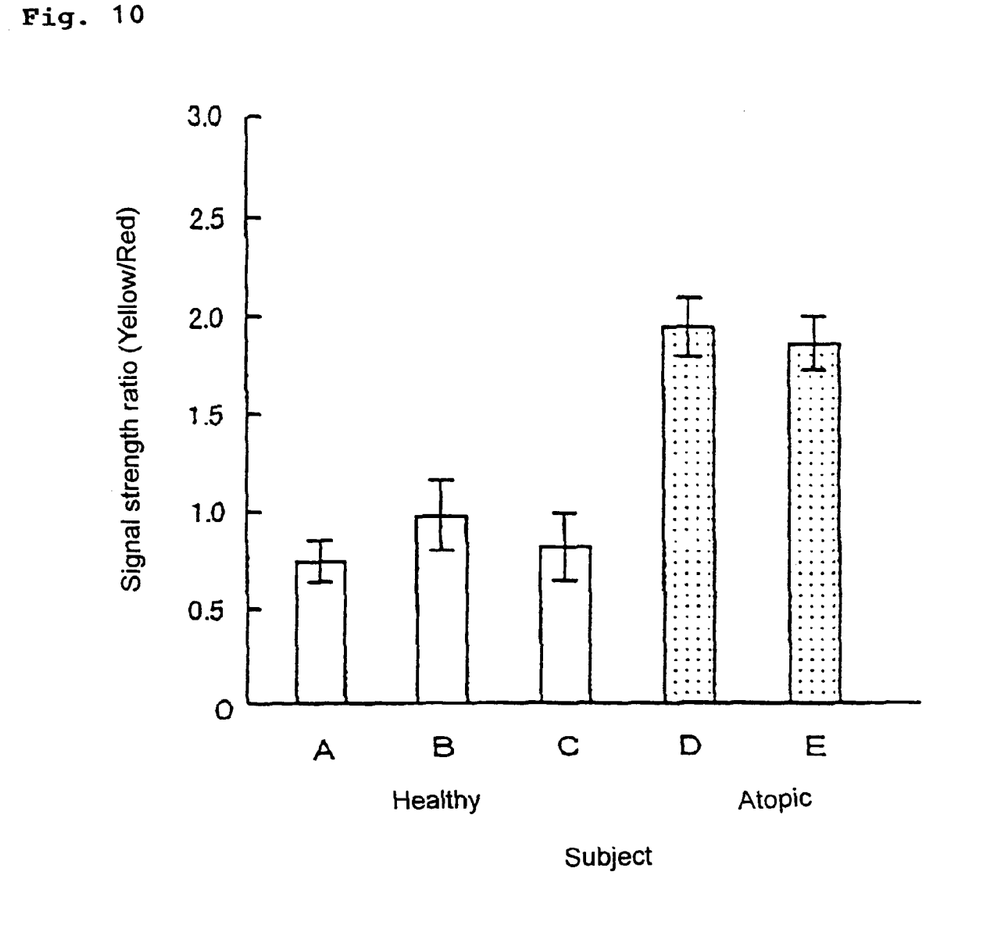
FIG. 10 diagrammatically illustrates average values of the strength ratio (Yellow/Red) between optic-acoustic signals as to individual subjects and standard deviations a thereof (in the drawing, 2σ is represented by I).

In FIG. 10, $x_2$ of the patients suffering from atopic dermatitis was higher than that of the healthy persons, and $\sigma_2$ was also small, so that each $x_2-\sigma_2$ of the two patients suffering from atopic dermatitis was higher than each $x_1+\sigma_1$ of the three healthy persons. For this reason, it is possible to evaluate skin conditions by calculating out the signal strength ratio between the respective coloring matters.

EXAMPLE 5

The mixed solution was applied in the same manner as in Example 4 except that the numbers of the healthy persons and patients suffering from atopic dermatitis were both reduced to 1. After 2 minutes, a pressure-sensitive adhesive tape was stuck on each of the applied sites to peel the horny layer, and the respective coloring matters were extracted with a 10% aqueous solution of ethanol to measure absorbance at 430 nm for Yellow Color No. 4 and at 545 nm for Red Color No. 215. Average values $x_3$ thereof and standard deviations $\sigma_3$ thereof, and an average value x4 of the ratio of the absorbance of Yellow Color No. 4 to the absorbance of Red Color No. 215, and a standard deviation $\sigma_4$ thereof are shown in Table 4.

TABLE 4

| | Yellow Color No. 4 | | Red Color No. 215 | | Yellow color No. 4/ Red Color No. 215 | |
|---|---|---|---|---|---|---|
| | $x_3$ | $\sigma_3$ | $x_3$ | $\sigma_3$ | $x_4$ | $\sigma_4$ |
| Healthy person | 0.0073 | 0.0019 | 0.0215 | 0.0052 | 0.340 | 0.041 |
| Patient of atopic dermatitis | 0.0089 | 0.0022 | 0.0183 | 0.0052 | 0.486 | 0.063 |

Since an error is great in absorbance as to each coloring matter, it is difficult to evaluate skin conditions from the absorbances of the respective coloring matters. However, the skin conditions can be evaluated when the ratio between the absorbances is calculated out.

EXAMPLE 6

The forearm of one of two healthy persons was subjected to a cleaning treatment (A/E treatment) with an organic solvent (ethyl ether/acetone =1:1) to artificially roughen the skin. With respect to the two subjects, the opto-acoustic signal strengths were measured in the same manner as in Example 4. Average values $x_5$ of the signal strengths in each subject and standard deviations $\sigma_5$ thereof, and an average value $x_6$ of the ratio (signal strength ratio) between the signal strength of Yellow Color No. 4 and the signal strength of Red Color No. 215 in each subject, and a standard deviation $\sigma_6$ thereof are shown in Table 5.

TABLE 5

| | Yellow Color No. 4 | | Red Color No. 215 | | Yellow color No. 4/ Red Color No. 215 | |
|---|---|---|---|---|---|---|
| | $x_5$ | $\sigma_5$ | $x_5$ | $\sigma_5$ | $x_6$ | $\sigma_6$ |
| Healthy person | 67.0* | 16.4 | 51.0* | 14.1 | 1.3 | 0.14 |
| Person subjected to A/E treatment | 55.0* | 12.9 | 20.0* | 4.6 | 2.8 | 0.64 |

*The unit of the numerical values is μV.

Since an error is great in signal strength as to each coloring matter, it is difficult to evaluate skin conditions from the signal strengths of the respective coloring matters. However, the skin conditions can be evaluated when the signal strength ratio is calculated out.

EXAMPLE 7

The peeled skin of a healthy Yucatan mini-swine (product of Charles River Japan Inc.) was used to subject it to the A/E treatment, thereby roughening the skin. As a control, the skin subjected to no A/E treatment was used. With respect to the two subject swines, the opto-acoustic signal strengths were measured in the same manner as in Example 4. Average values $x_7$ of the signal strengths in each subject swine and standard deviations $\sigma_7$ thereof and an average value $x_8$ of the ratio (signal strength ratio) between the signal strength of Yellow Color No. 4 and the signal strength of Red Color No. 215 in each subject swine, and a standard deviation $\sigma_8$ thereof are shown in Table 6.

TABLE 6

|  | Yellow Color No. 4 | | Red Color No. 215 | | Yellow color No. 4/ Red Color No. 215 | |
| --- | --- | --- | --- | --- | --- | --- |
|  | $x_7$ | $\sigma_7$ | $x_7$ | $\sigma_7$ | $x_8$ | $\sigma_8$ |
| Healthy swine | 55.0* | 12.6 | 31.0* | 7.4 | 1.8 | 0.19 |
| Swine subjected to A/E treatment | 154.0* | 36.2 | 60.0* | 14.1 | 2.6 | 0.36 |

*The unit of the numerical values is $\mu V$.

Since an error is great in signal strength as to each coloring matter, it is difficult to evaluate skin conditions from the signal strengths of the respective coloring matters. However, the skin conditions can be evaluated when the signal strength ratio is calculated out.

EXAMPLE 8

A mixed solution of 1,3-butanediol whose log P was 0.19, and glycerol-1-benzyl-3-n-hexyl diether whose log P was 3.66 was applied to each 5 sites of a healthy swine (Yucatan mini-swine) and a swine subjected to the A/E treatment In an amount of 200 $\mu l$ per $cm^2$. After 4 hours, a pressure-sensitive adhesive tape was stuck on each of the applied sites in each subject swine to peel the horny layer, and the respective chemical substances were extracted for 20 minutes with A/E to conduct determination by HPLC (ODS column). Average values xg of measured amounts in each subject swine and standard deviations $\sigma_9$ thereof, and an average value $x_{10}$ of the ratio of the measured amount of 1,3-butanediol to the measured amount of glycerol-1-benzyl-3-n-hexyl diether in each subject swine, and a standard deviation $\sigma_{10}$ thereof are shown in Table 7.

TABLE 7

|  | 1,3-Butanediol | | Glycerol-1-benzyl-3-n-hexyl diether | | 1,3-Butanediol/ glycerol-1-benzyl-3-n-hexyl diether | |
| --- | --- | --- | --- | --- | --- | --- |
|  | $x_9$ | $\sigma_9$ | $x_9$ | $\sigma_9$ | $x_{10}$ | $\sigma_{10}$ |
| Healthy swine | 510* | 122 | 630* | 148 | 0.81 | 0.091 |
| Swine subjected to A/E treatment | 980* | 249 | 710* | 174 | 1.38 | 0.19 |

*The unit of the numerical values is $\mu g/cm^2$.

Since an error is great in measured amount as to each chemical substance, it is difficult to evaluate skin conditions from the measured amounts as to the respective chemical substances. However, the skin conditions can be evaluated when the ratio therebetween is calculated out.

EXAMPLE 9

FAD, FMN and Rf were dissolved in water to give concentrations of 5.8 $mol/dm^3$, 0.48 $mol/dm^3$ and 0.011 $mol/dm^3$, respectively, thereby preparing a solution. The solution was applied to each 5 sites close to one another of a healthy swine (Yucatan mini-swine) and a swine subjected to the A/E treatment. After 2 minutes, a pressure-sensitive adhesive tape was stuck on each of the applied sites to peel the horny layer, and the respective chemical substances were extracted with a 1% SDS from the pressure-sensitive adhesive tape to measure absorbance at 420 nm, thereby determining the amounts of FAD, FMN and Rf penetrated. Average values $x_{11}$ of the amounts penetrated in each subject swine and standard deviations $\sigma_{11}$ thereof, an average value $x_{12}$ of the ratio of the absorbance of FMN to the absorbance of Rf, and a standard deviation $\sigma_{12}$ thereof, and an average value $x_{13}$ of the ratio of the absorbance of FAD to the absorbance of Rf and a standard deviation $\sigma_{13}$ thereof are shown in Table 8.

TABLE 1

|  | FAD | | FMN | | Rf | | FMN/Rf | | FAD/Rf | |
| --- | --- | --- | --- | --- | --- | --- | --- | --- | --- | --- |
|  | $x_{11}$ | $\sigma_{11}$ | $x_{11}$ | $\sigma_{11}$ | $x_{11}$ | $\sigma_{11}$ | $x_{12}$ | $\sigma_{12}$ | $x_{13}$ | $\sigma_{13}$ |
| Healthy swine | 0.375708 | 0.09017 | 0.215232 | 0.051656 | 0.042864 | 0.010287 | 5.0 | 0.58 | 8.8 | 1.01 |
| Swine subjected to A/E treatment | 0.292392 | 0.070174 | 0.230736 | 0.055377 | 0.017296 | 0.004151 | 13.3 | 1.53 | 16.9 | 1.61 |

The unit is $mg/cm^2$.

Since an error is great in absorbance as to each chemical substance, it is difficult to evaluate skin conditions from the absorbances as to the respective chemical substances. However, the skin conditions can be evaluated when the ratio between the absorbances of the respective chemical substances is calculated out.

EXAMPLE 10

The solution prepared in Example 9 was applied to subject swines in the same manner as in Example 9. Two minutes after from the application, opto-acoustic signal strengths of the respective subject swines were measured by the same method (wavelength of absorption spectrum: 460 nm) as in Example 1. Average values $x_{14}$ of the signal strengths at a concentration of 1 $mol/dm^2$ at 5 applied sites in each subject swine and standard deviations $\sigma_{14}$ thereof, an average value $x_{15}$ of the ratio of the signal strength of FMN to the signal strength of Rf and a standard deviation $\sigma_{15}$ thereof, and an average value $x_{16}$ of the ratio of the signal strength of FAD to the signal strength of Rf and a standard deviation $\sigma_{16}$ thereof are shown in Table 9.

TABLE 2

|  | FAD | | FMN | | Rf | | FMN/Rf | | FAD/Rf | |
| --- | --- | --- | --- | --- | --- | --- | --- | --- | --- | --- |
|  | $x_{14}$ | $\sigma_{14}$ | $x_{14}$ | $\sigma_{14}$ | $x_{14}$ | $\sigma_{14}$ | $x_{15}$ | $\sigma_{15}$ | $x_{16}$ | $\sigma_{16}$ |
| Healthy swine | 420 | 100.8 | 640 | 153.6 | 500 | 120 | 1.28 | 0.15 | 0.84 | 0.10 |
| Swine subjected to A/E treatment | 930 | 223.2 | 1240 | 297.6 | 610 | 146.4 | 2.03 | 0.23 | 1.52 | 0.18 |

The unit is $\mu v$

Since an error is great in opto-acoustic signal strength as to each chemical substance, it is difficult to evaluate skin conditions from the signal strengths as to the respective chemical substances. However, the skin conditions can be evaluated when the ratio between the signal strengths of the respective chemical substances is calculated out.

What is claimed is:

1. A method for evaluating skin conditions, comprising the steps of:

applying at least two chemical substances to skin;

measuring amounts of said at least two chemical substances penetrated into the skin; and calculating a ratio between the amounts of said at least two chemical substances penetrated into the skin.

2. The method according to claim 1, wherein the amounts of said at least two chemical substances penetrated into the skin are obtained by at least one of an opto-acoustic method, a chromatographic method, a color difference method and an absorptiometric method.

3. The method according to claim 1, wherein the amounts of the chemical substances penetrated into the skin are measured by an apparatus including irradiating means for irradiating the skin with excitation light and detecting means for detecting an acoustic signal generated in a medium provided in the apparatus by the skin.

4. A kit for evaluating skin conditions, comprising:

a reagent containing at least two chemical substances; and a measuring device configured to measure amounts of the at least two chemical substances penetrated into the skin;

wherein said at least two chemical substances are applied to the skin, amounts of said at least two chemical substances penetrated into the skin are measured by the measuring device, and a ratio between the amounts of said at least two chemical substances penetrated into the skin is calculated.

5. The kit according to claim 4, wherein the measuring device comprises an apparatus including irradiating means for irradiating the skin with excitation light and detecting means for detecting an acoustic signal generated in a medium provided in the apparatus by the skin.

6. An apparatus for measuring amounts of chemical substances penetrated into skin, comprising:

irradiating means for irradiating the skin with excitation light; and detecting means for detecting an acoustic signal generated in a medium provided in the apparatus by the skin;

wherein:

said irradiating means comprises at least one light emitting diode as a source of the excitation light; and the acoustic signal is used to evaluate conditions of the skin.

7. The apparatus according to claim 6, wherein:

said irradiating means comprises a plurality of light emitting diodes configured to emit lights having emission spectra which overlap with each other;

output controlling means for controlling output of the plurality of light emitting diodes to emit the lights concurrently; and an optical filter configured to pass rays within a prescribed wavelength range among the lights emitted from the plurality of light emitting diodes.

8. The apparatus according to claim 6, wherein the light emitting diode is driven at a duty ratio of 30 to 70%, and positioned adjacent to the skin such that an emission center of the light emitting diode is at a distance of 3 to 16 mm to the skin and the light emitting diode irradiates the skin in a diameter of 2 to 8 mm.

9. An apparatus for evaluating skin conditions, comprising the apparatus according to claim 6.

10. The apparatus according to claim 6, further comprising a controller configured to control modulation frequency of the excitation light according to a prescribed depth of measurement under the skin.

11. The apparatus according to claim 10, further comprising an oscillating circuit configured to produce the modulation frequency of the excitation light.

12. The apparatus according to claim 6, wherein said detecting means comprises a microphone.

* * * * *